(12) United States Patent
Nitz et al.

(10) Patent No.: US 8,945,891 B2
(45) Date of Patent: Feb. 3, 2015

(54) FERMENTATION PROCESS FOR PRODUCTION OF ACETONE, BUTANOL AND ETHANOL USING ISOPHORON AS ABSORBENT

(75) Inventors: Joerg-Joachim Nitz, Essen (DE); Gerda Grund, Coesfeld (DE); Franz Ulrich Becker, Freigericht-Horbach (DE); Patrick Stier, Grossostheim (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/124,486

(22) PCT Filed: Jun. 13, 2012

(86) PCT No.: PCT/EP2012/061141
§ 371 (c)(1),
(2), (4) Date: Dec. 6, 2013

(87) PCT Pub. No.: WO2012/171929
PCT Pub. Date: Dec. 20, 2012

(65) Prior Publication Data
US 2014/0113341 A1 Apr. 24, 2014

(30) Foreign Application Priority Data
Jun. 17, 2011 (DE) .......................... 10 2011 077 705

(51) Int. Cl.
*C12P 7/16* (2006.01)
(52) U.S. Cl.
USPC .......................... 435/160; 435/150; 435/161
(58) Field of Classification Search
USPC .......................... 435/150, 160, 161; 568/913
IPC ........................................ C12P 7/28,7/06, 7/16
See application file for complete search history.

(56) References Cited

U.S. PATENT DOCUMENTS

| 2005/0089979 | A1 | 4/2005 | Ezeji et al. | |
|---|---|---|---|---|
| 2009/0162912 | A1 | 6/2009 | Ezeji et al. | |
| 2010/0261237 | A1* | 10/2010 | Verseck et al. | 435/150 |
| 2010/0279370 | A1* | 11/2010 | Parten | 435/160 |
| 2012/0101304 | A1* | 4/2012 | Becker et al. | 568/382 |
| 2013/0261343 | A1 | 10/2013 | Orschel et al. | |

FOREIGN PATENT DOCUMENTS

| WO | WO 2009/056423 A2 | 5/2009 |
|---|---|---|
| WO | WO 2009/079362 A2 | 6/2009 |
| WO | WO 2010/121849 A1 | 10/2010 |
| WO | WO 2012/076314 A1 | 6/2012 |
| WO | WO 2012/156187 A1 | 11/2012 |

OTHER PUBLICATIONS

Colombo, et al., Liquid-Liquid Equilibria of the Ternary Systems Water + Acetic Acid + Ethyl Acetate and Water + Acetic Acid + Isophorone (3,5,5-Trimethyl-2-cyclohexen-1-one), Journal of Chemical and Engineering Data, vol. 44, No. 1, XP-002685675, 1999, pp. 35-39.
International Search Report issued Nov. 2, 2012, in PCT/EP12/061141 filed Jun. 13, 2012.
U.S. Appl. No. 14/116,233, filed Nov. 7, 2013, Orschel, et al.

\* cited by examiner

*Primary Examiner* — Ralph Gitomer
(74) *Attorney, Agent, or Firm* — Oblon, Spivak, McClelland, Maier & Neustadt, L.L.P.

(57) ABSTRACT

The invention relates to a method for producing a low-molecular-weight organic compound, such as acetone, butanol, and ethanol, in a fermentation process. The method contains a step of introducing a gas flow into an aqueous solution containing microorganisms producing the low-molecular-weight organic compound; a step of recovering the gas flow through a compound comprising isophoron; and optionally a step of separating the low-molecular-weight organic compound from the composition comprising isophoron.

16 Claims, No Drawings

FERMENTATION PROCESS FOR PRODUCTION OF ACETONE, BUTANOL AND ETHANOL USING ISOPHORON AS ABSORBENT

CROSS REFERENCE TO RELATED APPLICATIONS

The present application is a 35 U.S.C. §371 national stage patent application of International patent application PCT/EP2012/061141, filed on Jun. 13, 2012, published as WO/2012/171929 on Dec. 20, 2012, the text of which is incorporated by reference, and claims the benefit of the filing date of German application no. 10 2011 077 705.9, filed on Jun. 17, 2011, the text of which is also incorporated by reference.

FIELD OF THE INVENTION

The invention relates to a novel method for the inexpensive workup of low-molecular-weight products (molecular weight <100 g/mol), in particular acetone, butanol and ethanol, in a fermentation process. The workup succeeds by gas stripping combined with downstream absorption using isophorone as absorbent.

PRIOR ART

The solvents acetone, ethanol and butanol are important platform chemicals of the chemical industry with a constantly increasing demand. Especially for the production of acetone and butanol, currently mostly petrochemical methods are employed which are ultimately based on "cracking" petroleum and are therefore in the long term not forward-looking.

There is therefore great interest in developing alternative production methods based on carbon sources which look promising for the future such as, for example, from renewable raw materials, or even gaseous carbon sources, such as, e.g. carbon dioxide ($CO_2$) or carbon monoxide (CO). Fermentation processes can offer an alternative for producing platform chemicals, specialty chemicals and also fuel.

The greatest problem in most fermentative production methods is separating the organic product from the fermentation broth, since the broth is frequently highly complex and, especially, has a high water content. Large amounts of water are undesirable from the processing point of view, since the processing of a broth containing large amounts of water is energy consuming. The classical acetone-butanol-ethanol (ABE) fermentation using clostridia (e.g.: *Clostridium acetobutylicum*) is a microbial method for producing low-molecular-weight organic compounds and was utilized industrially as early as 1916 and delivers the products acetone-butanol-ethanol in the ratio 3:6:1 in the fermentation broth.

Qureshi and Blaschek, in *Renewable Energy*, 22(4): 557-564 and Ezeji et al., in Appl Microbiol Biotechnol, 63(6): 653-8, describe an ABE method in which the low-molecular-weight organic compounds are discharged from the fermentation broth by gas stripping and are adsorbed in cold traps.

This method has the disadvantage of a high energy demand, since the cooling must be maintained continuously. A further disadvantage is that in the cold traps, the products are only adsorbed inadequately, a considerable fraction is therefore discharged again from the trap and may be returned to the fermenter, as a result of which unwanted product inhibition can occur.

It was the object of the invention to provide a method which is able to permit a workup of the low-molecular-weight organic compounds from the aqueous fermentation broth using simple and energy-saving auxiliaries.

DESCRIPTION OF THE INVENTION

Surprisingly, it has been found that the method described hereinafter, which comprises absorption of the low-molecular-weight organic compounds using isophorone, is able to achieve the object of the invention.

The present invention therefore relates to a simple and inexpensive work-up method for fermentative production processes, wherein the products are removed from the fermentation broth in situ. The workup succeeds by means of gas stripping combined with a downstream absorption using isophorone and optionally subsequent separation into the pure components.

An advantage of the present invention is that the work-up method according to the invention can be applied both to anaerobic and aerobic fermentations. The gas stripping can therefore be carried out both with elemental oxygen-containing gases as carrier gas (in particular in processes under aerobic conditions), and with any elemental oxygen-free gases (in particular in processes under anaerobic conditions).

A further advantage of the present invention is that the low-molecular-weight organic compounds that are stripped out, particularly acetone, butanol and ethanol, in particular acetone can be concentrated (virtually) quantitatively by means of gas scrubbing in isophorone as absorbent.

A further advantage of the present invention is that the low-molecular-weight organic compounds can be separated again very simply from isophorone and therefore can be obtained in high purity.

Another advantage of the present invention is that the gases used for sustaining the microorganisms can simultaneously also adopt the function of the carrier gas; this applies in particular when the gases used have fractions of carbon dioxide, carbon monoxide, hydrogen, synthesis gas, or any desired mixtures of the abovementioned gases.

Furthermore, the present invention has the advantage that low-molecular-weight products can be removed from the fermentation broth in situ, and therefore high product concentrations cannot build up in the fermenter broth, which can have toxic effects on the microorganisms present.

The method according to the invention for producing low-molecular-weight organic compounds comprises the method steps A) providing an aqueous solution comprising microorganisms producing low-molecular-weight organic compounds,
B) introducing at least one gas or gas mixture into the aqueous solution,
C) channelling the gas stream out through an isophorone-containing composition and optionally
D) separating off the low-molecular-weight organic compounds from the isophorone-containing composition.

The expression "low-molecular-weight" is taken to mean the property of having a molecular weight <100 g/mol. All percentages (%) stated, are, unless stated otherwise, percent by mass. Unless stated otherwise, with regard to the ambient parameters such as pressure, temperature, standard conditions are meant.

Preferred low-molecular-weight organic compounds have a vapour pressure of greater than 3 hPa, preferably greater than 50 hPa, in particular greater than 150 hPa, at 20° C.

It is particularly preferred according to the invention that the low-molecular-weight organic compound is selected from the group comprising, preferably consisting of, acetone, butanol, ethanol, in particular acetone.

The microorganisms used in the method according to the invention, are, in particular, yeasts and bacteria. In particular, the microorganisms are selected from genera of the group comprising, preferably consisting of, *Clostridium, Zymomonas, Escherichia, Salmonella, Rhodococcus, Pseudomonas, Bacillus, Lactobacillus, Enterococcus, Acaligenes, Klebsiella, Paenibacillus, Arthrobacter, Corynebacterium, Brevibacterium, Pichia, Candida, Hansenula* and *Saccharomyces*. Exemplary species of these genera are *Escherichia coli, Alcaligenes eutrophus, Bacillus licheniformis, Paenibacillus macerans, Rhodococcus erythropolis, Pseudomonas putida, Enterococcus faecium, Enterococcus gallinarium, Enterococcus faecalis, Bacillus subtilis* and *Saccharomyces cerevisiae*.

In the method according to the invention, preferably a microorganism selected from the group *Escherichia coli, Cornybacterium glutamicum, Clostridium* spec., *Clostridium aceticum, Acetobacterium woodii, Clostridium acetobutylicum, Clostridium beijerinckii, Yarrowia lipolytica, Saccharomyces* spec., *Saccharomyces cerevisiae* and *Pichia pastoris* is used.

It is preferred according to the invention that the microorganisms are genetically modified microorganisms. In particular, here, the microorganisms used are those which have been genetically modified in such a manner that they are able to produce more low-molecular-weight organic compounds than the wild type thereof.

Such genetically modified microorganisms are described for producing acetone as low-molecular-weight organic compound in, for example, EP2181195. The cells disclosed in EP2181195 are preferably used in the method according to the invention for producing acetone. Such cells are suitable, in particular, for production methods under aerobic conditions.

Further such genetically modified microorganisms for producing acetone as low-molecular-weight organic compound are described in WO2010121849. The cells disclosed in WO2010121849 are preferably used in the method according to the invention for producing acetone, in particular in methods for production of acetone under anaerobic conditions.

Genetically modified microorganisms for producing butanol as low-molecular-weight organic compound are described, for example, in WO2008124523, WO2008052973 and WO2008052596. The cells disclosed in these applications are preferably used in the method according to the invention for producing butanol.

Genetically modified microorganisms for producing ethanol as low-molecular-weight organic compound are described, for example, in WO2011003893 and WO2010130806. The cells disclosed in these applications are preferably used in the method according to the invention for producing ethanol.

In the method according to the invention, in method step B), any desired gas or gas mixtures can be used as long as the gas or gas mixture does not enter into unwanted side reactions with the low-molecular-weight organic compounds, and is not toxic for the microorganisms used.

Preferably, the gas or gas mixture contains at least one selected from the group comprising, preferably consisting of, air, synthesis gas, nitrogen, carbon dioxide, carbon monoxide, hydrogen, oxygen and methane.

It is preferred according to the invention, as gas or gas mixtures in method step B), to use a gas or gas mixture containing elemental oxygen, if, in method step A), the microorganisms produce the low-molecular-weight organic compounds under aerobic conditions. The expression "aerobic condition", in the context of the present invention, is taken to mean that an oxygen partial pressure of >0.01 bar is present. In this context, the gas or gas mixture contains at least one selected from the group comprising, preferably consisting of, air or elemental oxygen.

It is preferred according to the invention, as gas or gas mixtures in method step B), to use a gas or gas mixture which is free from elemental oxygen if, in method step A), the microorganisms produce the low-molecular-weight organic compounds under anaerobic conditions. The expression "anaerobic condition", in the context of the present invention, is taken to mean that an oxygen partial pressure of ≤0.01 bar is present. In this context, the gas or gas mixture preferably contains at least one selected from the group comprising, preferably consisting of, synthesis gas, nitrogen, $CO_2$, CO, $H_2$ and methane.

In a further embodiment of the method according to the invention, the microorganisms used in method step A) are those which carry out the classical ABE fermentation in method step A); thus, in this context, the low-molecular-weight organic compounds are acetone, ethanol and butanol, in particular acetone. Such organisms which can be used classically in the ABE fermentation are *Clostridium acetobutylicum* and *Clostridium beijerinckii*, which multiply under strictly anaerobic conditions and convert mono-, di- and polysaccharides. The gas or gas mixture used in this method variant in method step B) is preferably at least one selected from the group comprising, preferably consisting of, nitrogen, air, synthesis gas, carbon dioxide, carbon monoxide, $H_2$ and methane.

In a further preferred variant of the method according to the invention, the microorganisms used in method step A) are acetogenic microorganisms which are able to form acetone as low-molecular-weight organic compound from at least one carbon source selected from the group containing carbon dioxide and carbon monoxide and the gas or gas mixture used in method step B) is at least one selected from the group comprising, preferably consisting of, nitrogen, synthesis gas, carbon dioxide, carbon monoxide and $H_2$. Cells that are preferably used in this method variant are described in WO 2010/121849.

In method step C), the low-molecular-weight organic compounds are conducted at least in part by channelling the gas stream out from the aqueous solution through an isophorone-containing composition. Preferably, the isophorone-containing composition contains of at least 50% by weight isophorone, preferably at least 80% by weight isophorone, particularly preferably at least 90% by weight isophorone, based on the total composition.

It is preferred according to the invention when the gas stream channelled out is passed through a plurality of spatially separated isophorone-containing compositions. The retention capacity can be increased thereby.

It is advantageous and preferred when the isophorone-containing composition present is cooled. As a result, more low-molecular-weight organic compound can be absorbed—based on the isophorone-containing composition. In this context, temperatures measured in the isophorone-containing composition are preferably in a range from −5° C. to 50° C., in particular from 0° C. to 30° C.

It is advantageous and therefore preferred when the gas or gas mixture leaving the isophorone-containing composition is fed back to the aqueous solution of method step A).

In method step D), the low-molecular-weight organic compounds are separated from the isophorone-containing composition, preferably by a pressure change and/or by a temperature elevation (>20° C. to <200° C.).

Thus, for example, the boiling points at atmospheric pressure are 56° C. for acetone, 100° C. for water, 215° C. for isophorone.

Therefore, in this context, for a system containing acetone and an isophorone-containing composition, the preferred temperatures are in a range from 20° C. to 75° C., in particular from 30° C. to 60° C., in order to separate the acetone from the isophorone-containing composition, wherein the temperature is measured in the isophorone-containing composition.

Pressures that are preferred in this context are in a range from 0 to 1.7 bar, particularly preferably 0.9 to 1.1 bar.

Particular preference is given in this context to a combination of atmospheric pressure (i.e. ambient pressure) and a temperature in the range from 30 to 60° C.

It is preferred according to the invention if at least the method steps B) and C) are carried out simultaneously with the production of the low-molecular-weight organic compound in method step A), in such a manner that this is a continuous in situ process, in which the product is discharged from the aqueous solution during or immediately after the formation.

In the examples discussed hereinafter, the present invention is described by way of example without limiting the invention. The scope of the entire description and the claims is not restricted to the embodiments cited in the examples.

The present invention further relates to the use of isophorone for absorption of low-molecular-weight organic compounds, preferably acetone, butanol, ethanol, in particular acetone, from a gas or gas mixture containing the low-molecular-weight organic compound, preferably acetone, butanol, ethanol, in particular acetone.

EXAMPLES

The isolation of organic compounds (acetone/ethanol/butanol) from an aqueous fermenter solution was studied. In all examples, a substantially aqueous fermenter solution having an organic fraction (e.g.: acetone/ethanol/butanol) of a maximum of 15% by weight was used, in order to strip out the organic components from the fermenter using a gas stream. Concluding purification and product isolation proceeded via separation by distillation.

Comparative Example 1, Not According to the Invention 1 liter of an aqueous solution having an organic fraction of 2.0% by weight acetone was charged into a 2 l fermenter. The fermenter was stirred at 200 rpm and treated with 0.6 volumes of stripping gas per volume of reactor per minute (vvm). As stripping gas, nitrogen was used, and the temperature of the fermenter solution was set to 34° C. Two cooling vessels were connected downstream of the fermenter in order to condense out and thus isolate the gaseous acetone. The collecting containers of the cooling vessels, for this purpose, were stored in dry ice at −78° C. and the coolers were cooled to 5° C.

On the basis of this experiment, it was found that acetone may be stripped out of the fermenter by means of a gas. After 5.5 h, only ~1.0% by weight acetone (~50% of the starting amount of acetone) were still present in the aqueous fermenter solution, and after 23 h only ~0.1% by weight acetone (~5% of the starting amount of acetone). The recovery rate of the stripped-out acetone in the cooled collecting containers of the cooling vessels was, however, only <40% after 23 h, i.e. more than 60% of the stripped acetone was not able to be collected and isolated in this manner.

Comparative Example 2, Not According to the Invention 1.4 liters of an aqueous solution having an organic fraction of 0.5% by weight acetone was charged to a 2 l fermenter. The fermenter was stirred at 500 rpm and treated with 0.2 volumes of stripping gas per volume of reactor per minute (vvm). As stripping gas, nitrogen was used, and the temperature of the fermenter solution was set to 30° C. Instead of the downstream cooling vessels, the gas stream was passed through six series-connected wash bottles filled with the solvent dimethyl sulphoxide (DMSO) which were connected downstream of the fermenter in order to absorb the gaseous acetone in DMSO. The first 5 wash bottles were filled with 200 g DMSO, the sixth wash bottle with 500 g of DMSO. Owing to the lower gas-treatment rate and the lower starting amount of acetone, as expected, the acetone was stripped out slower, after 23 h, ~0.28% by weight acetone (~55% of the starting amount of acetone), and after 48 h only ~0.13% by weight acetone (~27% of the starting amount of acetone) were still present in the aqueous fermenter solution. Using the series-connected DMSO solutions, the acetone recovery rate was improved, but this was still markedly too low. After 23 h, the recovery rate of the stripped acetone was less than 90%, and after 48 h, still only 74%.

Gas-stripping of acetone from an aqueous fermenter solution successful, but the absorption of the gaseous acetone in the solvent DMSO and thus the isolation of the acetone were inadequate.

Example 1, According to the Invention 0.3 liters of an aqueous solution having an organic fraction of 5% by weight acetone, 5% by weight ethanol and 5% by weight 1-butanol was charged into a 1 l fermenter. The fermenter was stirred at 200 rpm and treated with 0.1 volume of stripping gas per volume of reactor per minute (vvm). As stripping gas, nitrogen was used, and the temperature of the fermenter solution was set to 30° C. Instead of the downstream cooling vessels, the gas stream was passed through four series-connected wash bottles filled with the solvent isophorone which were connected downstream of the fermenter in order to absorb the gaseous acetone, ethanol and butanol in isophorone. The wash bottles were each filled with 300 g of isophorone. After 28 h, ~2.50% by weight acetone (~50% of the starting amount of acetone), 4.50% by weight ethanol (~90% of the starting amount of ethanol), and 4.60% by weight 1-butanol (~92% of the starting amount of butanol) were still present in the aqueous fermenter solution. After 68 h, ~0.76% by weight acetone (~15% of the starting amount of acetone), 4.03% by weight ethanol (~80% of the starting amount of ethanol) and 3.83% by weight 1-butanol (~76% of the starting amount of butanol) were still present in the aqueous fermenter solution. Using the series-connected isophorone solutions, the acetone-distinct recovery rate was improved, and also the recovery rates for ethanol and 1-butanol were markedly >90%. After 28 h, the recovery rate of the stripped acetone was >93%, of the stripped ethanol was >95%, and of the stripped 1-butanol was >96%. After 68 h, the recovery rate of the stripped acetone was >92%, of the stripped ethanol was >93%, and of the stripped 1-butanol was >94%.

Gas-stripping of acetone, ethanol and butanol from an aqueous fermenter solution successful. Isolation of the organic components (acetone, ethanol, 1-butanol) by absorption in the solvent isophorone successful. A virtually quantitative recovery rate was able to be achieved thereby.

Example 2, According to the Invention

In order to obtain the acetone, ethanol and butanol dissolved in isophorone as pure substances, such a mixture was separated by distillation. For this purpose liters of an acetone-ethanol-butanol mixture (5% by weight in each case) dissolved in isophorone were made up and separated by distillation at atmospheric pressure, the reflux ratio of the column was 8:1 here. The boiling points at atmospheric pressure were, for acetone, 56° C., for ethanol 78° C., for 1-butanol 118° C., and isophorone 215° C. In this case not only virtually pure acetone, but also pure ethanol and butanol phases were obtained. The purity level of the individual isolated phases was here up to >99% purity.

Therefore, it is possible to expel the acetone/ethanol/butanol generated in the fermenter in situ from the fermenter by gas stripping, to dissolve the gaseous acetone/ethanol/butanol (absorbate) in liquid isophorone (absorbent) and finally obtain the acetone/ethanol/butanol via separation by distillation.

The invention claimed is:

1. A method for producing a low-molecular-weight organic compound, the method comprising
   A) introducing at least one gas or gas mixture into an aqueous solution comprising microorganisms producing the low-molecular-weight organic compound, which is acetone, butanol, or ethanol,
   B) channeling the gas or gas mixture out through a composition comprising isophorone, and optionally
   C) separating the low-molecular-weight organic compound from the composition comprising isophorone.

2. The method of claim 1, wherein the microorganisms are selected from genera of the group consisting of *Clostridium, Zymomonas, Escherichia, Salmonella, Rhodococcus, Pseudomonas, Bacillus, Lactobacillus, Enterococcus, Acaligenes, Klebsiella, Paenibacillus, Arthrobacter, Corynebacterium, Brevibacterium, Pichia, Candida, Hansenula* and *Saccharomyces*.

3. The method of claim 1, wherein the gas or gas mixture comprises at least one gas selected from the group consisting of air, synthesis gas, nitrogen, carbon dioxide, carbon monoxide, hydrogen, oxygen and methane.

4. The method of claim 1, wherein
   the microorganisms are *Clostridium acetobutylicum* or *Clostridium beijerinckii* and
   the gas or gas mixture comprises at least one gas selected from the group consisting of nitrogen, air, synthesis gas, carbon dioxide, carbon monoxide, $H_2$ and methane.

5. The method of claim 1, wherein
   the low-molecular-weight organic compound is acetone, and
   the microorganisms are microorganisms that produce acetone starting from acetyl coenzyme A acetone via an enzymatic reaction of acetyl-CoA to form acetoacetyl-CoA,
   an enzymatic reaction of acetoacetyl-CoA to form acetoacetate and coenzyme A, wherein the coenzyme A is not transferred to an acceptor molecule, and
   decarboxylation of acetoacetate to form acetone and $CO_2$.

6. The method of claim 1, wherein
   the low-molecular-weight organic compound is acetone,
   the microorganisms are acetogenic microorganisms that form acetone from at least one carbon source selected from the group consisting of carbon dioxide and carbon monoxide, and
   the gas or gas mixture comprises at least one gas selected from the group consisting of nitrogen, synthesis gas, carbon dioxide, carbon monoxide and $H_2$.

7. The method of claim 1, wherein the gas or gas mixture channeled out in B) is passed through a plurality of spatially separated compositions comprising isophorone.

8. The method of claim 1, wherein the gas or gas mixture leaving the composition comprising isophorone is fed back to the aqueous solution of A).

9. The method of claim 1, wherein, in A), the microorganisms produce the low-molecular-weight organic compound under aerobic conditions, and the gas or gas mixture comprises elemental oxygen.

10. The method of claim 1, wherein, in A), the microorganisms produce the low-molecular-weight organic compound under anaerobic conditions, and the gas or gas mixture comprises no elemental oxygen.

11. The method of claim 1, wherein the low-molecular weight organic compound is acetone.

12. The method of claim 1, wherein the low-molecular weight organic compound is butanol.

13. The method of claim 1, wherein the low-molecular weight organic compound is ethanol.

14. The method of claim 1, wherein the composition comprising isophorone comprises isophorone at a content of at least 50% by weight, based on a total weight of the composition.

15. The method of claim 1, wherein, in B), the composition comprising isophorone is maintained at a temperature of from −5° C. to 50° C.

16. The method of claim 1, wherein A) and B) are carried out simultaneously with the production of the low-molecular-weight organic compound.

* * * * *